United States Patent

Murata et al.

[11] 4,338,170
[45] Jul. 6, 1982

[54] ISOMERIZATION OF β-γ-UNSATURATED ALCOHOL OR ITS ESTER

[75] Inventors: Atsuo Murata; Syuji Tsuchiya; Hideo Suzuki, all of Funabashi, Japan

[73] Assignee: Nissan Chemical Industries, Ltd., Tokyo, Japan

[21] Appl. No.: 152,819

[22] Filed: May 23, 1980

[30] Foreign Application Priority Data

Jun. 14, 1979 [JP] Japan .................................. 54-74936
Nov. 2, 1979 [JP] Japan ............................... 54-142419
Nov. 2, 1979 [JP] Japan ............................... 54-142421

[51] Int. Cl.³ ...................... B01J 19/08; C07C 35/00; C07C 67/333; C07C 69/76
[52] U.S. Cl. ............................ 204/158 R; 260/405.6; 560/67; 560/71; 560/112; 560/113; 560/179; 560/183; 560/189; 560/224; 560/225; 560/249; 560/261; 560/262; 568/875; 568/906
[58] Field of Search ................... 204/158 R; 568/875, 568/906; 560/249, 261, 224, 225, 262, 112, 113, 67, 71, 183, 179, 189; 260/405.6

[56] References Cited

U.S. PATENT DOCUMENTS 2,979,445  4/1961  Lavigne et al. ................ 204/158 R
4,105,700  8/1978  Fujita et al. ......................... 568/875

Primary Examiner—Howard S. Williams
Attorney, Agent, or Firm—Oblon, Fisher, Spivak, McClelland & Maier

[57] ABSTRACT

A cis-trans isomerization of a cis-β-γ-unsaturated alcohol or its ester having the formula

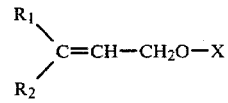

wherein $R_1$ represents hydrogen atom or a $C_1$–$C_5$ alkyl group; X represents hydrogen atom or

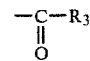

and $R_2$ represents a hydrocarbon moiety or a hydroxyhydrocarbon moiety; $R_3$ represents hydrogen atom or a hydrocarbon moiety into a transform, in the presence of a mercaptan as a catalyst, is provided. It can be also attained in the presence of a mercaptan and/or a disulfide as a catalyst in an inert gas environment with an initiator. It can be also attained in the presence of a mercaptan under an irradiation, if desired with a small amount of an initiator.

5 Claims, No Drawings

ISOMERIZATION OF β-γ-UNSATURATED ALCOHOL OR ITS ESTER

BACKGROUND OF THE INVENTION

1. Field of the Invention

The present invention relates to a process for isomerization of β-γ-unsaturated alcohol or its ester. More particularly, it relates to a process for cis-trans isomerization of a β-γ-unsaturated alcohol or its ester especially from a cis-form to a trans-form β-γ-unsaturated alcohol or its ester.

2. Description of the Prior Art

It has been known to carry out a cis-trans isomerization of β-γ-unsaturated alcohol in the presence of an acidic catalyst (Japanese Patent Publication 8107/1963) and in the presence of a transition metal type catalyst (Japanese Unexamined Patent Publication 2940/1976).

There is no prior art for a cis-trans isomerization of β-γ-unsaturated ester.

In the conventional cis-trans isomerization of β-γ-unsaturated alcohol, expensive reagent is required or a preparation of the catalyst is complicate or a separation and reuse of the catalyst is not easy. These processes are disadvantageous in an industrial process. It has disadvantages of a shift of the double bond or a shift of hydroxy group in the isomerization even though it can be employed as an industrial process. It has been difficult to attain the selective cis-trans isomerization even though it can be employed as an industrial process. When an acidic catalyst or an alkaline catalyst is used for the isomerization of β-γ-unsaturated ester, a shift of the double bond is performed to be difficult to attain the selective cis-trans isomerization.

The inventors have studied cis-trans isomerizations of β-γ-unsaturated alcohols or its esters to overcome the difficulties.

SUMMARY OF THE INVENTION

It is an object of the present invention to provide a selective cis-trans isomerization of β-γ-unsaturated alcohol or its ester without a shift of the double bond.

It is another object of the present invention to provide a cis-trans isomerization of β-γ-unsaturated alcohol or its ester at high velocity and high selectivity.

The foregoing and other objects of the present invention have been attained by a cis-trans isomerization of a cis-β-γ-unsaturated alcohol or its ester having the formula

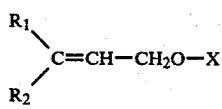

wherein $R_1$ represents hydrogen atom or a $C_1$–$C_5$ alkyl group; X represents hydrogen atom or

and $R_2$ represents a hydrocarbon moiety or a hydroxyhydrocarbon moiety; $R_3$ represents hydrogen atom or a hydrocarbon moiety into a trans-form, in the presence of a mercaptan as a catalyst. It can be also attained in the presence of a mercaptan and/or a disulfide as a catalyst in an inert gas environment with an initiator. It can be also attained in the presence of a mercaptan under an irradiation, if desired with a small amount of an initiator.

DETAILED DESCRIPTION OF THE PREFERRED EMBODIMENTS

The mercaptans used in the present invention include non-substituted or substituted aromatic mercaptans such as benzenethiol, o-, m- or p- toluenethiols and chlorothiophenol; and alkyldithiols such as decyldithiol and octyldithiol; and other mercaptans such as thioglycol and mercaptoethanol (referred to as Mercaptan (I)); and the other mercaptans such as octylthiol, cyclohexanethiol and cyclopentanethiol (referring to as Mercaptan (II)). The catalyst can be also dialkylsulfides such as diphenyldisulfide and dioctyldisulfide. When the Mercaptan (II) or disulfide is used as a catalyst, it is necessary use a small amount of an initiator in an inert gas. When the Mercaptan (I) is used as the catalyst, it is possible to perform the isomerization without any initiator in the atmosphere.

Suitable inert gases include rare gases such as helium and argon gases, nitrogen and hydrogen gases.

Suitable initiators include radical initiators such as azobisisobutyronitrile (AIBN) and benzoyl peroxide (BPO).

Suitable unsaturated alcohols used in the present invention include hydroxynerol (3,7-dimethyl-2 octene-1,7-diol) and nerol (3,7-dimethyl-2,6-octadiene-1-ol); farnesol (3,7,11-trimethyl-2,6,10-dodecatriene-1-ol);phytol(3,7,11,15-tetramethyl-2-hexadecene-1-ol); and crotyl alcohol (2-butene-1-ol). It is not critical to use them.

Suitable unsaturated esters used in the present invention include esters obtained by the condensation of the following alcohol and the following carboxylic acid. The alcohols can be hydroxynerol, nerol, farnesol, phytol and crotyl alcohol. The carboxylic acids can be saturated or unsaturated aliphatic acid such as formic acid, acetic acid, propionic acid, caproic acid, butyric acid, acrylic acid, and pentenoic acid; aromatic carboxylic acids such as benzoic acid (it is possible to have hydroxy group, in said hydrocarbon group of the carboxylic acid).

The catalyst used in the process of the present invention is easily available with a low cost and is effective for a selective cis-trans isomerization. The separation and reuse of the catalyst can be carried out by a simple operation. Therefore, the industrial value is remarkably high.

In accordance with the process of the present invention, the trans-form unsaturated alcohol or its ester is easily obtained at high selectivity from the cis-form unsaturated alcohol or its ester.

The by-products may be also useful. For example, citral and citronellal useful as a perfume or a source of perfume can be obtained from nerol. A low boiling component or a large molecular weight compound as a by-product are remarkably small.

A ratio of the catalyst to the unsaturated alcohol or its ester as the source is preferably in a range of 0.1 to 100 wt.% especially 0.5 to 50 wt.%. When the ratio of the catalyst is more than 50 wt.% it is not economical whereas when it is less than 0.5 wt.% a reaction velocity is not high enough.

A ratio of the initiator to the unsaturated alcohol or its ester is preferably in a range of 0.1 to 20 wt.%, especially 1 to 10 wt.%. The reaction can be performed at a ratio of higher than 20 wt.% it is not economical whereas when it is less than 0.1 wt.%, the effect of the addition of the initiator is not remarkable.

The reaction temperature can be in a range of 20° to 250° C. especially 40° to 200° C. When it is lower than 20° C., the reaction velocity is low whereas when it is higher than 250° C., the selectivity is low.

When an irradiation is carried out in the presence of mercaptan if desired with an initiator, an isomerization of a cis-$\beta$-$\gamma$-unsaturated alcohol or its ester can be performed at low temperature such as 0° to 50° C. at high velocity.

The light sources are preferably a high pressure mercury discharge lamp or a xenon discharge lamp.

When a small amount of a radical initiator is incorporated in the photoisomerization, the selectivity is slightly lower, however, the cis-trans isomerization is performed at remarkably high velocity. It is several times of the isomerization velocity to that of the incorporation of only the mercaptan.

At the temperature of 0° to 50° C. for the process of the invention, the cis-trans isomerization velocity is remarkably slow except irradiating it in the presence of the mercaptan and the radical initiator. In accordance with the incorporation of the radical initiator and the mercaptan under the irradiation, the remarkable effect is attained though the mechanism is not clarified.

A molar ratio of the radical initiator to the mercaptan is in a range of 0.01 to 0.2.

The process of the present invention is remarkably effective, because the reaction mixture does not substantially absorb light and accordingly, the photoenergy can be remarkably small and a photoreactor can be simple to be easily designed. The reaction at high concentration is easily performed and any side reaction such as a shift of the double bond or a shift of the functional group is not found except a formation of a small amount of a high boiling compound, and accordingly, a purification by a separation of the object compound is easily carried out after the reaction.

The irradiation is performed at a degree high enough to give an excited state which is easily found by a simple experiment.

The irradiation is preferably performed by a mercury discharge lamp having a power of 100 Watt to 10 KWatt. The discharge lamp can be dipped in the reaction mixture though it can be placed with a gap from the reaction mixture. The distance is preferably short such as 100 mm to several mm.

The reaction can be selectively performed without any solvent. Thus, the selectivity can be further improved by using the specific solvent.

Suitable solvents include saturated alcohols such as ethanol, butanol, hexanol, octanol and decanol; saturated hydrocarbons such as octane, decane and tridecane; and aromatic hydrocarbons such as benzene, toluene and xylene.

The photoisomerization as one embodiment of the present invention will be illustrated.

The process of the present invention is not a photosensitizing reaction and a mercaptan does not absorb light. Therefore, the mercaptan is not a photosensitizer, but is an additive for accelerating the photoisomerization. The mechanism for the cis-trans photoisomerization has not been clarified. A cis-trans isomerization is not easily performed without an irradiation even though a mercaptan is added to the unsaturated compound, and it is not easily performed without an addition of a mercaptan even though an irradiation is applied.

By the irradiation in the presence of a mercapatan, the cis-form is converted into the trans-form, at high selectivity.

After the isomerization, the catalyst can be separated by a simple distillation or a chemical separation with a dilute alkaline aqueous solution, if necessary, further a precise distillation so as to separate the cis-form and the trans-form for the purification.

The present invention will be further illustrated by certain examples and references which are provided for purposes of illustration only and are not intended to be limiting the present invention.

EXAMPLE 1

An isomerization of 30 g. of nerol was carried out in the presence of 3 g. of thiophenol at 60° C. for 3 hours. The reaction mixture was analyzed by a gas chromatography. As a result, a conversion of nerol was 33%. A selectivity to geraniol as the transform alcohol was 74%. A selectivity to citronellal as a by-product was 11%.

EXAMPLE 2 to 10

In accordance with the process of Example 1 except varying the condition for the isomerization as shown in Table 1, each isomerization was carried out. When a solvent was used, two times of the solvent to nerol was used. The results are shown in Table 1.

TABLE 1

| Exp. | Catalyst | Solvent | React. temp. (°C.) | React. time (hr.) | Conv. of nerol (%) | Selectivity (%) geraniol | Selectivity (%) citronellal |
|---|---|---|---|---|---|---|---|
| 2 | CH$_3$——SH | — | 50 | 3.5 | 28 | 72 | 11 |
| 3 | But—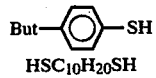—SH | — | 50 | 4.5 | 36 | 70 | 13 |
| 4 | HSC$_{10}$H$_{20}$SH | — | 100 | 2.5 | 13 | 68 | 0 |
| 5 | HOC$_2$H$_4$SH | — | 80 | 3 | 15 | 80 | trace |
| 6 | HOOCCH$_2$SH | — | 60 | 2.3 | 32 | 75 | 0 |
| 7 | 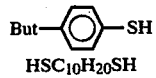—SH | xylene | 70 | 3 | 34 | 90 | 5 |
| 8 | " | ethylene glycol | 70 | 4.5 | 32 | 82 | 13 |

TABLE 1-continued

| Exp. | Catalyst | Solvent | React. temp. (°C.) | React. time (hr.) | Conv. of nerol (%) | Selectivity (%) geraniol | Selectivity (%) citronellal |
|---|---|---|---|---|---|---|---|
| 9 | " | n-octanol | 70 | 5.5 | 33 | 80 | 3 |
| 10 | " | tridecane | 70 | 3.3 | 30 | 77 | trace |

EXAMPLE 11

An isomerization of 30 g. of nerol was carried out in the presence of 6 g. of n-octyl mercaptan and 0.3 g of azobisisobutyronitrile at 100° C. for 30 minutes with stirring in a nitrogen atmosphere. The reaction mixture was analyzed by a gas chromatography. A conversion of nerol was 33%. A selectivity to geraniol as the transform alcohol was 91%. A selectivity to citral as the by-product was 1%.

EXAMPLES 12 to 22

In accordance with the process of Example 11 except using two times of each solvent to nerol and varying the kind of the catalyst and the condition as shown in Table 2, each isomerization was carried out. The results are shown in Table 2'.

TABLE 2

| Exp. | Catalyst | Cat./nerol (wt/wt) | AIBN/nerol (wt/wt) | Solvent | Solv./nerol (wt/wt) | Temp. (°C.) | Time (hr.) |
|---|---|---|---|---|---|---|---|
| 12 | n-C$_8$H$_{17}$SH | 0.2 | AIBN/nerol 0.01 | —*1 | — | 80 | 4.5 |
| 13 | " | 0.2 | AIBN/nerol 0.04 | n-octanol | 2 | 80 | 3 |
| 14 | " | 0.2 | AIBN/nerol 0.04 | xylene | 2 | 100 | 0.7 |
| 15 | " | 0.05 | AIBN/nerol 0.04 | xylene | 2 | 80 | 6 |
| 16*2 | " | 0.2 | AIBN/nerol 0.04 | xylene | 2 | 80 | 2.2 |
| 17 | " | 0.05 | BPO/nerol 0.04 | xylene | 2 | 80 | 3 |
| 18 | n-C$_{10}$H$_{21}$SH | 0.2 | AIBN/nerol 0.04 | xylene | 2 | 80 | 2.5 |
| 19 | —SH | 0.2 | AIBN/nerol 0.04 | xylene | 2 | 80 | 4 |
| 20 | HSC$_{10}$H$_{20}$SH | 0.05 | AIBN/nerol 0.04 | —*1 | — | 80 | 1.5 |
| 21 | —SH | 0.01 | AIBN/nerol 0.04 | xylene | 2 | 80 | 1 |
| 22 | 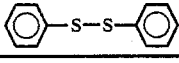 | 0.2 | AIBN/nerol 0.04 | —*1 | — | 70 | 4.4 |

Note:
*1 no solvent
*2 in H$_2$ gas flow
AIBN azoisobutyronitrile
BPO benzoyl peroxide

TABLE 2'

| Exp. | Conversion of nerol | Selectivity (%) geraniol | citral | citronellal |
|---|---|---|---|---|
| 12 | 43 | 90 | t | t |
| 13 | 51 | 93 | t | 2 |
| 14 | 50 | 93 | t | t |
| 15 | 42 | 95 | 2 | t |
| 16 | 49 | 94 | t | — |
| 17 | 32 | 94 | 3 | — |
| 18 | 48 | 95 | — | t |
| 19 | 27 | 96 | — | t |
| 20 | 32 | 93 | 3 | 1 |
| 21 | 31 | 93 | t | 4 |
| 22 | 20 | 73 | 8 | 7 |

Note:
t: trace

REFERENCE 1

In accordance with the process of Example 11 except adding 1.5 g. of n-octyl mercaptan without azobisisobutyronitrile and reacting for 1 hour in air flow, the isomerization of nerol was carried out. As a result, a conversion of nerol was 44%. A selectivity to geraniol was 33%. A selectivity to citral was 2%.

EXAMPLE 23

An isomerization of neryl acetate was carried out in the presence of 1.5 g. of thiophenol at 80° C. for 17 hours with stirring in the atmosphere. The reaction mixture was analyzed by a gas chromatography. As a result, a conversion of neryl acetate was 47%. A selectivity to geranyl acetate as the trans-form ester was 84%.

EXAMPLES 24 to 27

In accordance with the process of Example 23 except varying the reaction environment, the initiator, azobisisobutyronitrile (AIBN), the amount of the solvent and the other condition as shown in Table 3, each isomerization was carried out. The result are shown in Table 3'.

TABLE 3

| Exp. | Catalyst cat./ NeOAc (wt/wt) | Environment | AIBN AIBN/ NeOAc (wt/wt) | Solvent solv./ NeOAc (wt/wt) | Temp. (°C.) | Time (hr.) |
|---|---|---|---|---|---|---|
| 24 | ⟨○⟩—SH, 0.05 | Atm. | —*1 | n-octanol 2 | 80 | 2 |
| 25 | ⟨○⟩—SH, 0.05 | N₂ gas | 0.02 | —*2 | 80 | 2 |
| 26 | n-C₈H₁₇SH, 0.05 | " | 0.04 | —*2 | 80 | 1.5 |
| 27 | ⟨○⟩—SH, 0.05 | " | 0.04 | n-octanol 2 | 80 | 2 |

Note:
NeOAc: neryl acetate
*1AIBN is not added
*2no solvent

TABLE 3'

| Exp. | Conversion of NeOAc (%) | Selectivity to GeOAc (%) |
|---|---|---|
| 24 | 60 | 90 |
| 25 | 51 | 88 |
| 26 | 46 | 87 |
| 27 | 55 | 93 |

Note:
GeOAc: geranyl acetate

EXAMPLE 28

Nerol (cis-3,7-dimethyl-2,6-octadiene-1-ol) and each mercaptan were dissolved in benzene at each concentration of 0.05 mole/liter. Each solution was bubbled with nitrogen gas in a Pyrex glass tube and then the tube was sealed. The tube with the solution was irradiated by a high pressure mercury discharge lamp (250 watt) at the ambient temperature from a distance of 5.5 cm. After the irradiation, nerol and geraniol (trans-3,7-dimethyl-2,6-octadiene-1-ol) in the reaction mixture were analyzed by a gas chromatography.

The results of the isomerizations of nerol in the presence of each of various mercaptans are shown in Table 4.

TABLE 4

| Kind of mercaptan | Reaction time (min.) | Conversion of nerol (%) | Selectivity to geraniol (%) |
|---|---|---|---|
| n-laurylmercaptan | 50 | 40 | 100 |
| n-decylmercaptan | 15 | 50 | 100 |
| n-decylmercaptan | 30 | 63 | 84 |
| t-nonylmercaptan | 60 | 34 | 83 |
| n-hexylmercaptan | 30 | 50 | 97 |
| n-hexylmercaptan | 60 | 60 | 85 |
| cyclohexylmercaptan | 30 | 58 | 85 |

EXAMPLE 29

In accordance with the process of Example 28 except varying each concentration of n-decylmercaptan as the additive, a photoisomerization of nerol was carried out. The results are shown in Table 5.

TABLE 5

| Concentration of n-decylmercaptan (mole/liter) | Reaction time (min.) | Conversion of nerol (%) | Selectivity to geraniol (%) |
|---|---|---|---|
| 0.025 | 30 | 55 | 87 |
| 0.005 | 30 | 30 | 100 |
| 0.005 | 60 | 48 | 85 |

EXAMPLE 30

In accordance with the process of Example 28 except using the equal mole of n-decylmercaptan as the additive to nerol and irradiating for 30 minutes and varying the concentration of nerol, a photoisomerization of nerol was carried out. The results are shown in Table 6.

TABLE 6

| Concentration of nerol (mole/liter) | Conversion of nerol (%) | Selectivity to geraniol (%) |
|---|---|---|
| 0.05 | 63 | 84 |
| 0.1 | 63 | 70 |
| 0.5 | 54 | 73 |
| 1 | 43 | 90 |
| 2 | 24 | 90 |

EXAMPLE 31

In accordance with the process of Example 28, a photoisomerization of nerol was carried out by directly irradiating to a mixture of nerol and n-decylmercaptan at an equal mole without benzene as the solvent. After the irradiation for 30 minutes, a conversion of nerol was 25% and a selectivity to geraniol was 90%. After the irradiation for 60 minutes, a conversion of nerol was 48% and a selectivity to geraniol was 60%.

EXAMPLE 32

In accordance with the process of Example 31 except using n-hexylmercaptan as the additive, a photo isomerization of nerol was carried out. After the irradiation for 60 minutes, a conversion of nerol was 37% and a selectivity to geraniol was 77%.

EXAMPLE 33

In accordance with the process of Example 6 except dissolving nerol and n-decylmercaptan into benzene at each concentration of 0.05 mole/liter and dissolving AIBN at a concentration of 0.0025 mole/liter, a photoisomerization of nerol was carried out. After the irradiation for 10 minutes, a conversion of nerol was 50% and a selectivity to geraniol was 85%.

EXAMPLE 34

In accordance with the process of Example 33 except using BPO instead of AIBN, a photoisomerization was carried out. After the irradiation for 3 minutes, a conversion of nerol was 48%, and a selectivity to geraniol was 92%. After the irradition for 10 minutes, a conversion of nerol was 62% and a selectivity to geraniol was 85%.

In all of the examples, any alcohol in which the double bond is shifted or OH group is shifted was not found. Any consumption of the mercaptan was not found.

We claim:

1. In an isomerization of a cis-$\beta$-$\gamma$-unsaturated alcohol or its ester having the formula:

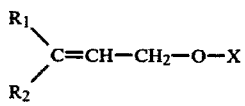

wherein

R$_1$ represents hydrogen atom or a C$_1$-C$_5$ alkyl group;
x represents hydrogen atom or —C(O)—R$_3$;
R$_2$ represents a hydrocarbon moiety or a hydroxy hydrocarbon moiety; and
R$_3$ represents hydrogen atom or a hydrocarbon moiety, into a trans-form; the improvement characterized by isomerizing said cis-$\beta$-$\gamma$-unsaturated alcohol or ester in the presence of a mercaptan or disulfide, which is a member selected from the group consisting of aromatic mercaptans, alkyl dithiols, dialkyl disulfides, thioglycol, mercaptoethanol, octylthiol, cyclohexanethiol, cyclopentanethiol, and mixtures thereof, as a catalyst;
wherein said isomerization occurs substantially without shift of the double bond from said $\beta$-$\gamma$-unsaturated position.

2. The process according to claim 1 wherein said isomerization is carried out in an inert gas environment with an initiator.

3. In an isomerization of a cis $\beta$-$\gamma$-unsaturated alcohol or its ester having the formula;

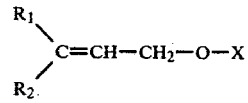

wherein

R$_1$ represents hydrogen atom or a C$_1$-C$_5$ alkyl group;
X represents hydrogen atom or —C(O)—R$_3$;
R$_2$ represents a hydrocarbon moiety or a hydroxy hydrocarbon moiety; and
R$_3$ represents hydrogen atom or a hydrocarbon moiety, into a trans-form, the improvement characterized by isomerizing said cis $\beta$-$\gamma$-unsaturated alcohol or ester in the presence of a mercaptan or disulfide which is a member selected from the group consisting of aromatic mercaptans, alkyl dithiols, dialkyl disulfides, thioglycol, mercaptoethanol, octylthiol, cyclohexanethiol, cyclopentanethiol, and mixtures thereof as a catalyst; wherein said isomerization is carried out under irradiation.

4. The process according to claim 3 wherein said cis-trans isomerization is carried out in the presence of a mercaptan and a small amount of an initiator under an irradiation.

5. The process of claim 3 wherein said irradiation is from a high pressure mercury discharge lamp or a xenon discharge lamp.

* * * * *